(12) United States Patent
Engheta et al.

(10) Patent No.: US 8,293,087 B2
(45) Date of Patent: Oct. 23, 2012

(54) SYSTEM AND METHOD FOR CONTROLLING NANOPARTICLES USING DIELECTROPHORETIC FORCES

(75) Inventors: Nader Engheta, Berwyn, PA (US); Brian Edwards, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 1146 days.

(21) Appl. No.: 12/158,365

(22) PCT Filed: Dec. 21, 2006

(86) PCT No.: PCT/US2006/049071
§ 371 (c)(1),
(2), (4) Date: Jun. 20, 2008

(87) PCT Pub. No.: WO2008/051248
PCT Pub. Date: May 2, 2008

(65) Prior Publication Data
US 2008/0289965 A1 Nov. 27, 2008

Related U.S. Application Data

(60) Provisional application No. 60/753,320, filed on Dec. 21, 2005.

(51) Int. Cl.
*G01N 27/26* (2006.01)
*G01N 27/447* (2006.01)
(52) U.S. Cl. ........................................ 204/547; 204/643
(58) Field of Classification Search .................. 204/547, 204/643
See application file for complete search history.

(56) References Cited

U.S. PATENT DOCUMENTS

| 5,814,200 A | 9/1998 | Pethig et al. |
| 6,150,089 A | 11/2000 | Schwartz |
| 6,341,237 B1 * | 1/2002 | Hurtado ........................ 607/148 |

(Continued)

FOREIGN PATENT DOCUMENTS

WO WO 2004/076060 * 9/2004

OTHER PUBLICATIONS

Edwards et al., "Theory of simultaneous control of orientation and translational motion of nanorods using positive dielectrophoretic forces", J. of Applied Physics, Dec. 15, 2005, 98(12), 124314.1-124314.7.

(Continued)

*Primary Examiner* — Jeffrey T Barton
*Assistant Examiner* — Jennifer Dieterle
(74) *Attorney, Agent, or Firm* — Woodcock Washburn LLP

(57) ABSTRACT

The present invention is directed to the use of dielectrophoretic forces for the arbitrary manipulation of micrometer- and nanometer-sized particles and to devices capable of arbitrarily manipulating micrometer- and nanometer-sized particles by means of dielectrophoretic forces within a two- or three-dimensional region. The devices and methods of the invention are capable of arbitrarily controlling the velocities, locations, and forces applied to a particle, arbitrarily specifying a force or set of forces at a location in space, and determining friction and/or drag coefficients of a particle, and are thus well-suited for a range of applications including cell sorting, drug delivery, as a diagnostic tool for determining membrane stiffness, and in the heterogeneous integration of micro- and nano-components through directed assembly.

26 Claims, 8 Drawing Sheets

U.S. PATENT DOCUMENTS

| | | | |
|---|---|---|---|
| 6,492,175 B1 * | 12/2002 | Muller et al. | 435/450 |
| 6,576,459 B2 | 6/2003 | Miles et al. | |
| 2003/0015428 A1 * | 1/2003 | Becker et al. | 204/547 |
| 2003/0047456 A1 * | 3/2003 | Medoro | 204/547 |
| 2004/0053290 A1 * | 3/2004 | Terbrueggen et al. | 435/6 |
| 2004/0067502 A1 * | 4/2004 | Guenther et al. | 435/6 |

OTHER PUBLICATIONS

Gosse et al., "Magnetic Tweezers: Micromanipulation and Force Measurement at the Molecular Level", Biophys J., Jun. 2002, 82(6), 3314-3329.

* cited by examiner

US 8,293,087 B2

SYSTEM AND METHOD FOR CONTROLLING NANOPARTICLES USING DIELECTROPHORETIC FORCES

CROSS-REFERENCE TO RELATED APPLICATIONS

The present application is a 371 national phase entry application of PCT/US2006/049071 filed Dec. 21, 2006, which also claims benefit of U.S. Provisional Patent Application No. 60/753,320 filed Dec. 21, 2005. The contents of these applications are incorporated herein by reference.

BACKGROUND OF THE INVENTION

The manipulation of individual submicron-sized objects has been the focus of significant efforts over the last few years. Specifically, efforts have been made toward developing touchless electromagnetic positioning systems for micrometer- and nanometer-sized particles. As opposed to micromanipulators and atomic force microscopy, touchless technologies represent a different approach to the application of controlled forces to small particles while simultaneously removing the difficulties of other approaches such as, for example, stiction. Developments in lab-on-a-chip technologies, heterogeneous integration of electronic components, and studies in nanofluidics are among many which are driven, in large part, by the rate of innovation in their tools, and these technologies and others would derive significant benefit from developments in positioning systems for micrometer- and nanometer-sized particles.

Various tools have emerged to fill this need. The most well known are optical tweezers which use a finely focused laser as the electromagnetic source to allow the arbitrary positioning of very small objects. Optical tweezers have the ability to specify a location in space by focusing a laser beam. Positively polarizable particles are attracted to this region. This is very useful for manipulating positively polarizable objects. Since the beam represents a region of attraction, there is no need for negative feedback.

Magnetic tweezers have recently been reported in which a magnetic particle is controlled using the magnetic field generated by an array of coils. See, for example, C. Gosse and V. Croquette, Biophys J 82, 3314-3329 (2002), the disclosure of which is incorporated herein by reference. While optical tweezers allows for such manipulation, resolution is limited due to physical constraints on laser spot size. The beam is very localized and the force that is applied is indirect. That is, when the particle drifts to the outer edge of the focus, it feels an attraction back, but quantifying the applied force is difficult. Additionally atomic force microscopy can be used to position nanoscale particles but involves a complex apparatus. Magnetic tweezers also allow arbitrary positioning of particles, but this approach is constrained to magnetic entities.

Electric fields have remained very attractive because of the ease with which they are generated on very small scales with microelectrode structures. Many electrokinetic techniques have emerged such as positive dielectrophoresis, negative dielectrophoresis, traveling wave dielectrophoresis, and electrorotation. While particles have been manipulated within the space between electrodes, it has not been done arbitrarily. Unlike the arbitrary positioning of optical and magnetic tweezers, these techniques have only been used to direct particles toward or away from electrodes. The use of electrodes in this fashion "discretizes" the affected space so that the particles can only be controlled with a spatial resolution similar to that of the electrode array itself. These techniques are thus limited to accuracies defined by the electrode spacings themselves.

SUMMARY OF THE INVENTION

The present invention is directed to the use of dielectrophoretic forces for manipulation of micrometer- and nanometer-sized particles. Broadly framed, this approach enables the arbitrary manipulation of an arbitrary number of particles within a two or three dimensional region defined by an electrode array using dielectrophoretic forces. While the orientations of the individual particles are readily controlled through the angle of the electric field, their positions can be indirectly manipulated through an applied force. The conditions that the field must satisfy at the position of each particle that will produce the desired individual motion and orientation of each particle can be derived. A desired orientation and force can be imposed on N particles providing that there are at least 4N+1 electrodes, and this manipulation can be accomplished under realistic conditions within a region of reasonable dimension. This technique combines the low cost of electrokinetic devices with the flexibility of optical and magnetic tweezers.

BRIEF DESCRIPTION OF THE DRAWINGS

FIG. 8(a) shows a dispersion of rods before the electrodes are activated, and FIG. 8(b) shows the single remaining rod (under the cursor) after they are activated. Note that the indicated rod is "balanced" so that in the several seconds that elapsed between the two figures, all other rods move to nearby electrodes. The relative position of one circle to that of the other circle indicates the direction and magnitude of the applied force, and the direction of the line in the cursor indicates the direction of the applied electric field.

DETAILED DESCRIPTION OF THE INVENTION

According to one aspect of the invention, there is provided an apparatus for using dielectrophoretic forces for the manipulation of micrometer- and nanometer-sized particles. This apparatus may be used to control the forces applied to such a particle while observing its motion to determine its drag coefficients. Using drag coefficients, force can be related to velocity. The apparatus can thus be used to control particle velocity. Additionally, the particle can be directed to move across a preprogrammed path. In one embodiment, the apparatus comprises an electric tweezers.

Electric tweezers specify a force to be applied at a location in space. For a reasonable distance around the particle, the applied force can be held constant. As a result, electric tweezers are suitable as a force probe as small displacements or errors in localizing the particle do not dramatically affect the applied force.

As used herein, "nanoparticle" is meant to include particles of regular or irregular morphology having an average diameter of at least about 20 nm. Examples of suitable nanoparticle shapes include spheroids, ellipsoids, rods, discs, and the like. With regard to composition, suitable nanoparticles include all nanoparticles which are capable of responding to electromagnetic forces as described herein by having a complex permittivity different from that of the surrounding medium. Exemplary nanoparticles are gold nanorods and suitably-sized biological materials such as cells, bacteria and the like.

A particle location, desired orientation, and force can be directly related to a set of electrode voltages. This method makes several simplifying assumptions concerning the experimental geometry. While the orientation of each particle is directly specified through the angle of the local electric field, its position is indirectly controlled through the applied force. Each electrode is approximated as an unknown point charge and an induced dipole. Since each induced dipole results from the combination of all other sources, a set of linear constraints are derived to enforce the self-consistency of the system. Additionally, the force and orientation of each particle also form an additional set of linear constraints. This combined set of constraints is then solved numerically to yield the sources required to induce the desired orientation and motion of each particle. The minimum number of electrodes that can be used to control a set of N particles is 4N+1. Numerical simulations demonstrate that the control of a single nanorod in the midst of a realistic electrode array can be accomplished under practical conditions. In addition, such control of orientation and motion can be achieved over an ample region in the vicinity of each rod.

Figure 1:
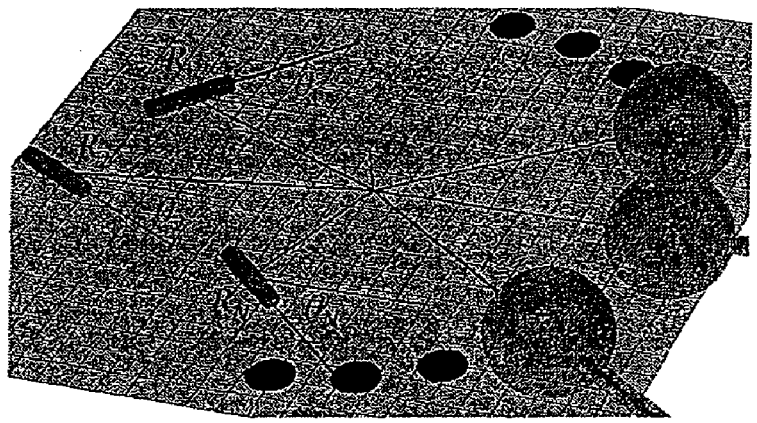
FIG. 1 shows an embodiment of the invention comprising an array of n electrodes at positions $\vec{r}_1$ through $\vec{r}_n$ in the same plane as a nanorod at position $\vec{R}$. Black dots represent continuation of the pattern.

As shown in FIG. 1, an applied electric field generated by a set of electrodes in the same plane as the particles is used to control the position and orientation of a set of polarizable rod-shaped particles. Each rod can be modeled as an induced dipole at location $\vec{R}_j$, where j goes from 1 to N, and possesses a polarizability $\alpha_{rod}$ that is negligible in all directions except along its axis. A potential energy minimum exists with respect to orientation when the rod is aligned with the local electric field. Assuming that the field changes slowly enough so that all inertial and drag terms are negligible, controlling the orientation of the rod is therefore readily accomplished by controlling the direction of the electric field, $\vec{E}$, at that location. In the following discussion, the rod is indeed assumed to be oriented along the field, allowing the dipole moment to be introduced as $\vec{p}_{rod} = \alpha_{rod}\vec{E}$.

It would be convenient if there was an analogous method for controlling the position of the particle, i.e. through a potential energy minimum with respect to the spatial coordinates. However, such direct control is physically impossible for the reasons outlined below.

The potential energy U of a single dipole is given by $$U = -\vec{P}_{rod} \cdot \vec{E} = -\alpha_{rod}(\vec{E} \cdot \vec{E})\big|_{R_j} \quad (1)$$

$$= -\alpha_{rod}\left(\left(\frac{\partial V}{\partial x}\right)^2 + \left(\frac{\partial V}{\partial y}\right)^2 + \left(\frac{\partial V}{\partial z}\right)^2\right)\bigg|_{R_j},$$

where V is the voltage field. The existence of an energy minimum would require that the first derivatives of the potential energy be equal to zero with respect to all directions, and that the second derivatives be positive with respect to all directions. It is sufficient to show that $$\mathrm{Max}\left[\frac{\partial^2 U}{\partial x^2} + \frac{\partial^2 U}{\partial y^2} + \frac{\partial^2 U}{\partial z^2}\right] \leq 0 \quad (2)$$

to prove that it is impossible to simultaneously satisfy $\partial^2 U/\partial x^2 > 0$, $\partial^2 U/\partial y^2 > 0$, and $\partial^2 U/\partial z^2 > 0$, and thus impossible to create a potential energy minimum with respect to space. If the field is static and in a source free region, it must also satisfy Laplace's equation:

$$\frac{\partial^2 V}{\partial x^2} + \frac{\partial^2 V}{\partial y^2} + \frac{\partial^2 V}{\partial z^2} = 0. \quad (3)$$

By taking the first derivatives of Laplace's equation to get three linear constraints, Eq. (2) is constrained by $$\frac{\partial^3 V}{\partial x^3}\bigg|_{R_j} + \frac{\partial^3 V}{\partial x \partial y^2}\bigg|_{R_j} + \frac{\partial^3 V}{\partial x \partial z^2}\bigg|_{R_j} = 0 \quad (4)$$

$$\frac{\partial^3 V}{\partial y \partial x^2}\bigg|_{R_j} + \frac{\partial^3 V}{\partial y^3}\bigg|_{R_j} + \frac{\partial^3 V}{\partial y \partial z^2}\bigg|_{R_j} = 0$$

-continued $$\frac{\partial^3 V}{\partial z \partial x^2}\bigg|_{\vec{R}_j} + \frac{\partial^3 V}{\partial x \partial y^3}\bigg|_{\vec{R}_j} + \frac{\partial^3 V}{\partial z^3}\bigg|_{\vec{R}_j} = 0.$$

By expressing potential energy in Eq. (2) in terms of the voltage field through Eq. (1), treating each of the local derivatives to be the variables, and maximizing the goal function in Eq. (2) by changing these variables under the constraints in Eq. (4), it can be shown that $$\text{Max}\left[\frac{\partial^2 U}{\partial x^2} + \frac{\partial^2 U}{\partial y^2} + \frac{\partial^2 U}{\partial z^2}\right] = 0, \quad (5)$$

and, therefore, it is impossible to contain an induced dipole in a source free region with a static field.

This mathematical disparity requires derivation of two distinct approaches to the orientation and the position of the dipole. To control the orientation, the desired electric field angle needs to be specified locally. However, the position must be controlled by inducing motion through an applied force. Additionally, the first derivatives of the voltage field are now defined in terms of the orientation of the dipole and the magnitude of the applied electric field needed to hold that orientation:

$$\cos(\theta)_j E_0 = -\frac{\partial V}{\partial x}\bigg|_{\vec{R}_j} \quad (6)$$

$$\sin(\theta_j) E_0 = -\frac{\partial V}{\partial y}\bigg|_{\vec{R}_j}.$$

Taking the negative gradient of the potential energy and assuming that the dipole and all sources are contained in the x,y-plane so that $(\partial V/\partial z)|_{z=0}=0$, we obtain the force on the rod $$\vec{F}_j = \left(2\alpha_{rod}\left(\frac{\partial V}{\partial x}\frac{\partial^2 V}{\partial x^2} + \frac{\partial V}{\partial y}\frac{\partial^2 V}{\partial x \partial y}\right)\bigg|_{\vec{R}_j}\right)\vec{\alpha}_x + \left(2\alpha_{rod}\left(\frac{\partial V}{\partial x}\frac{\partial^2 V}{\partial y \partial x} + \frac{\partial V}{\partial y}\frac{\partial^2 V}{\partial y^2}\right)\bigg|_{\vec{R}_j}\right)\vec{\alpha}_y. \quad (7)$$

The electric field can be defined in polar coordinates at the location of a rod by a magnitude $E_0$ and an angle $\theta_j$. Making this transformation and separating the two components of Eq. (6) yields $$F_{jx} = -2\alpha_{rod} E_0\left(\cos(\theta_j)\frac{\partial^2 V}{\partial x^2} + \sin(\theta_j)\frac{\partial^2 V}{\partial x \partial y}\right)\bigg|_{\vec{R}_j} \quad (8)$$

$$F_{jy} = -2\alpha_{rod} E_0\left(\cos(\theta_j)\frac{\partial^2 V}{\partial y \partial x} + \sin(\theta_j)\frac{\partial^2 V}{\partial y^2}\right)\bigg|_{\vec{R}_j}.$$

For a dipole at $\vec{R}_j$, there are now four conditions through Eqs. (7) and (8) that the field must locally satisfy based on the desired orientation of the dipole, an applied field magnitude, and a force vector.

From an understanding of the force and orientation of a single rod in a local electric field follows the problem of controlling an ensemble of rods, each at a position $\vec{R}_j$, where j goes from 1 to N. To satisfy each of the four constraints for each of the N dipoles, one would generally require at least 4N independent parameters that can be individually specified. This is accomplished by creating the electric field using n electrodes where $n \geq 4N$. Assume that each electrode i can be approximated as a point charge ($q_i$) and an induced dipole ($p_{xi}$ and $p_{yi}$) due to the fields generated by all other electrodes. Although it is ultimately the voltage on each electrode that will be experimentally controlled, it is more tractable to use those sources as mathematically intermediate quantities. The contributions of the charge and dipole at $\vec{r}_i$ to the voltage field at $\vec{R}_j$ follow as $$q_i G_q[\vec{R}_k, \vec{r}_i] = q_i \frac{1}{4\pi\varepsilon|\vec{R}_k - \vec{r}_i|}, \quad (6)$$

$$p_{xi} G_{p_x}[\vec{R}_k, \vec{r}_i] = p_{xi} \frac{(\vec{R}_k - \vec{r}_i) \cdot \vec{a}_x}{4\pi\varepsilon|\vec{R}_k - \vec{r}_i|^3}, \quad (7)$$

and $$p_{yi} G_{p_y}[\vec{R}_k, \vec{r}_i] = p_{yi} \frac{(\vec{R}_k - \vec{r}_i) \cdot \vec{a}_y}{4\pi\varepsilon|\vec{R}_k - \vec{r}_i|^3}. \quad (8)$$

Note that $\vec{R}_k$ could be either the location of another electrode ($\vec{r}_k$), or a rod ($\vec{R}_k$). The induced dipole on an electrode i is proportional the electric field at $\vec{R}_i$. Therefore, all the charges and dipoles are interrelated and the following relations must be satisfied in order to create a self-consistent system. For i ranging from 1 to n, $\vec{p}_i = \alpha_i \cdot \vec{E}|_{\vec{r}_i}$ must be true. Consequently, by examining x and y components of the electric field, all the sources are constrained by $$0 = \frac{p_{xi}}{\alpha_{xi}} + \sum_{\substack{j=1 \\ j \neq i}}^{n} (q_j \partial_x G_q[\vec{r}_i, \vec{r}_j] + p_{xj} \partial_x G_{p_x}[\vec{r}_i, \vec{r}_j] + p_{yj} \partial_x G_{p_y}[\vec{r}_i, \vec{r}_j]) \quad (9)$$

$$0 = \frac{p_{yi}}{\alpha_{yi}} + \sum_{\substack{j=1 \\ j \neq i}}^{n} (q_j \partial_y G_q[\vec{r}_i, \vec{r}_j] + p_{xj} \partial_y G_{p_x}[\vec{r}_i, \vec{r}_j] + p_{yj} \partial_y G_{p_y}[\vec{r}_i, \vec{r}_j]).$$

Higher order sources will add similar constraints and are considered within the scope of the present invention.

The charges and dipoles can be used to determine the voltage required on each electrode. Providing that the capacitance of the electrode i is $C_i$, the voltage on each electrode $V_i$ is $$V_i = q_i / C_i + \sum_{\substack{j=1 \\ j \neq i}}^{n} (q_j G_q[\vec{r}_i, \vec{r}_j] + p_{xj} G_{p_x}[\vec{r}_i, \vec{r}_j] + p_{yj} G_{p_y}[\vec{r}_i, \vec{r}_j]) \quad (13)$$

where i ranges goes from 1 to n. Eqs. (12) and (13) can be used to form a linear relation between a set of sources, such as for example $q_i$, $p_{xi}$ and $p_{yi}$, and a set of electrode voltages, such as for example $V_i$, to form $V = (_v M_s) \cdot S$. This relation can be inverted to form $S = (_s M_v) \cdot V$ where $S = \{q_1 p_{x1} p_{y1}, q_2 p_{x2} p_{y2}, \ldots, q_n p_{xn} p_{yn}\}$ and $V = \{V_1, V_2, \ldots, V_n\}$, or similarly extrapolated to higher dimensions.

The approximate voltage at the location $\vec{R}_j$ of a given particle can be defined as $$V[\vec{R}_j] = \sum_{i=1}^{n} \left( q_i G_q[\vec{R}_j, \vec{r}_i] + p_{xi} G_{p_x}[\vec{R}_j, \vec{r}_i] + p_{yi} G_{p_y}[\vec{R}_j, \vec{r}_i] \right). \quad (14)$$

where it was assumed that $\vec{R}_j$ is located at some reasonable distance from all electrodes. For each rod j ranging from 1 to N, employing the above approximation in Eqs. (7) and (8) yields $$\cos(\theta_j) E_0 = -\partial_x V[\vec{R}_j] = A_{j1} \cdot S = A_{j1} \cdot (_sM_v) \cdot V \sin(\theta_j) E_0 = -\partial_y V[\vec{R}_j] = A_{j2} \cdot S = A_{j2} \cdot (_sM_v) \cdot V \quad (15)$$

and $$F_{jx} = -2\alpha_{rod} E_0 (\cos(\theta_j) \partial_{x,x} V[\vec{R}_j] + \sin(\theta_j) \partial_{x,y} V[\vec{R}_j]) = A_{j3} \cdot S = A_{j3} \cdot (_sM_v) \cdot V$$

$$F_{jy} = -2\alpha_{rod} E_0 (\cos(\theta_j) \partial_{y,x} V[\vec{R}_j] + \sin(\theta_j) \partial_{y,y} V[\vec{R}_j]) = A_{j4} \cdot S = A_{j4} \cdot (_sM_v) \cdot V. \quad (16)$$

Initially employing four times as many electrodes as there are rods (i.e. n=4N), Eqs. (15) and (16) result in a system of 4N equations and 4N unknowns that can be numerically solved for the charge and dipole on each of the n electrodes.

Figure 2:
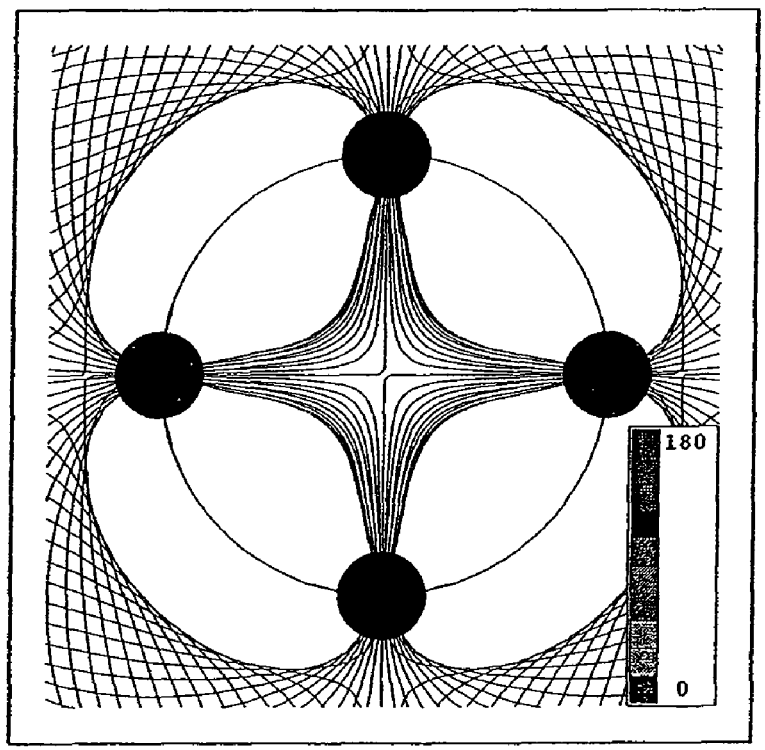
FIG. 2 shows an embodiment of the invention comprising a four-electrode system in which the network of lines represents positions of indeterminacy.

While n=4N electrodes will generally satisfy those conditions, some pathological situations do exist that would actually require using n>4N electrodes. Consider a matrix, M, formed from the coefficients vectors of the right hand sides of Eqs. (15) and (16). When the determinant of M is zero, it will be impossible to find a set of charges and dipoles satisfying an arbitrary orientation and force vector. This matrix is a function of the position and the orientation of the rod and yields a whole region in which no solution exists for some combination of position and orientation when solely using 4N electrodes to specify the orientation and force of a single (N=1) particle as shown in FIG. 2.

Figure 3:
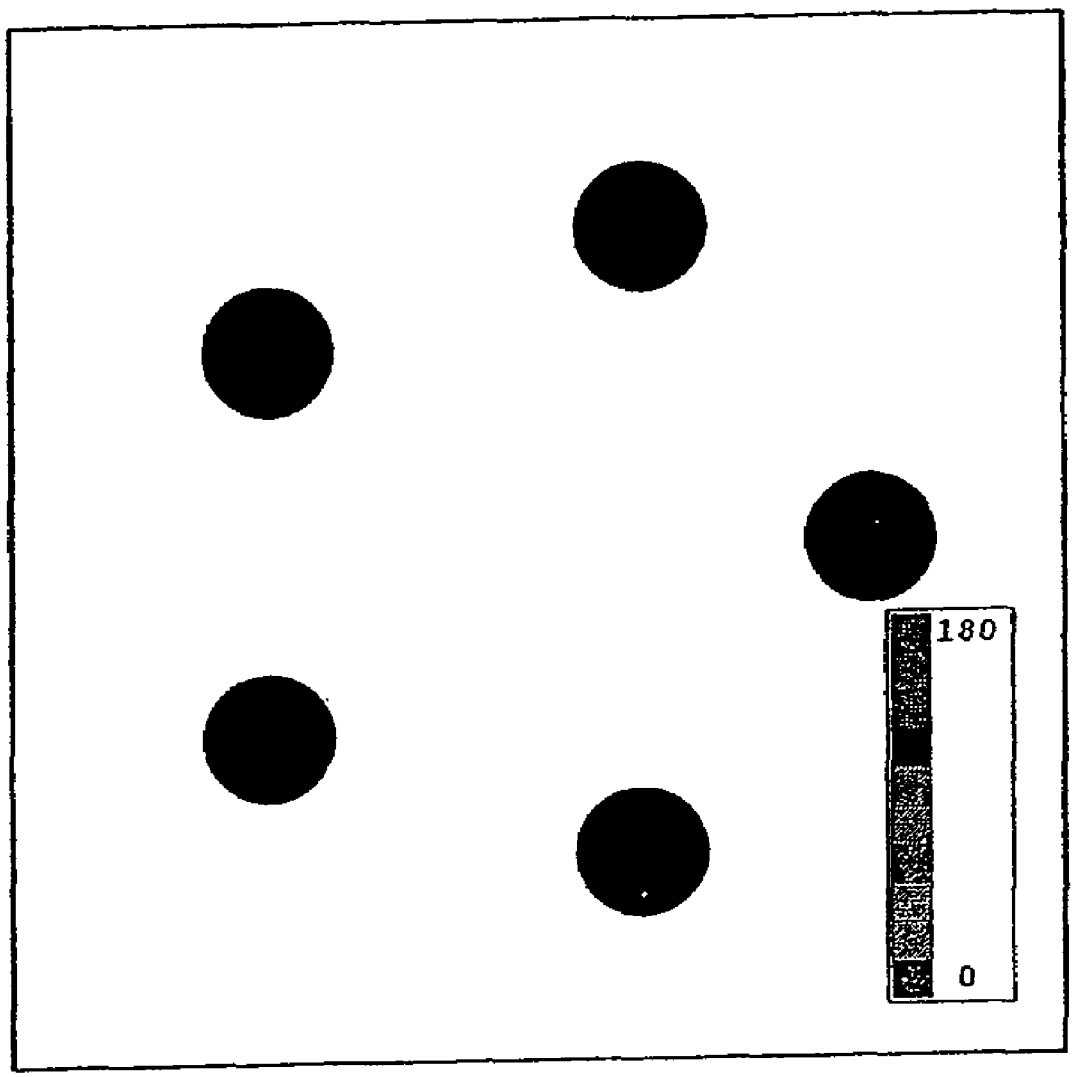
FIG. 3 shows an embodiment of the invention comprising a completely determined five-electrode system.

For example, consider a rod located at the exact center of four electrodes arranged at the points of a compass. If the rod is to be oriented along the east-west axis, there must be no component of the electric field in the north-south direction at the rod's location. Therefore, the north and south electrodes must be at the same voltage. However, if one wishes to apply a northerly force on the rod while maintaining this orientation, the north and south electrodes must be at different voltages to disrupt the symmetry. It is therefore impossible to maintain this orientation while moving the rod off this axis. While this example is intuitively obvious, one can find lines in the x-y plane for every orientation in which it is impossible to generate an arbitrary force. Greater than 4N electrodes may be used to find no such pathological cases as shown in FIG. 3. This leads to an under-constrained problem that can be solved using minimization of some experimentally important quantity such as, for example, (V·V), leading to a set of voltages that will provide the desired force and orientation on N rods with minimal voltages.

Figure 4:
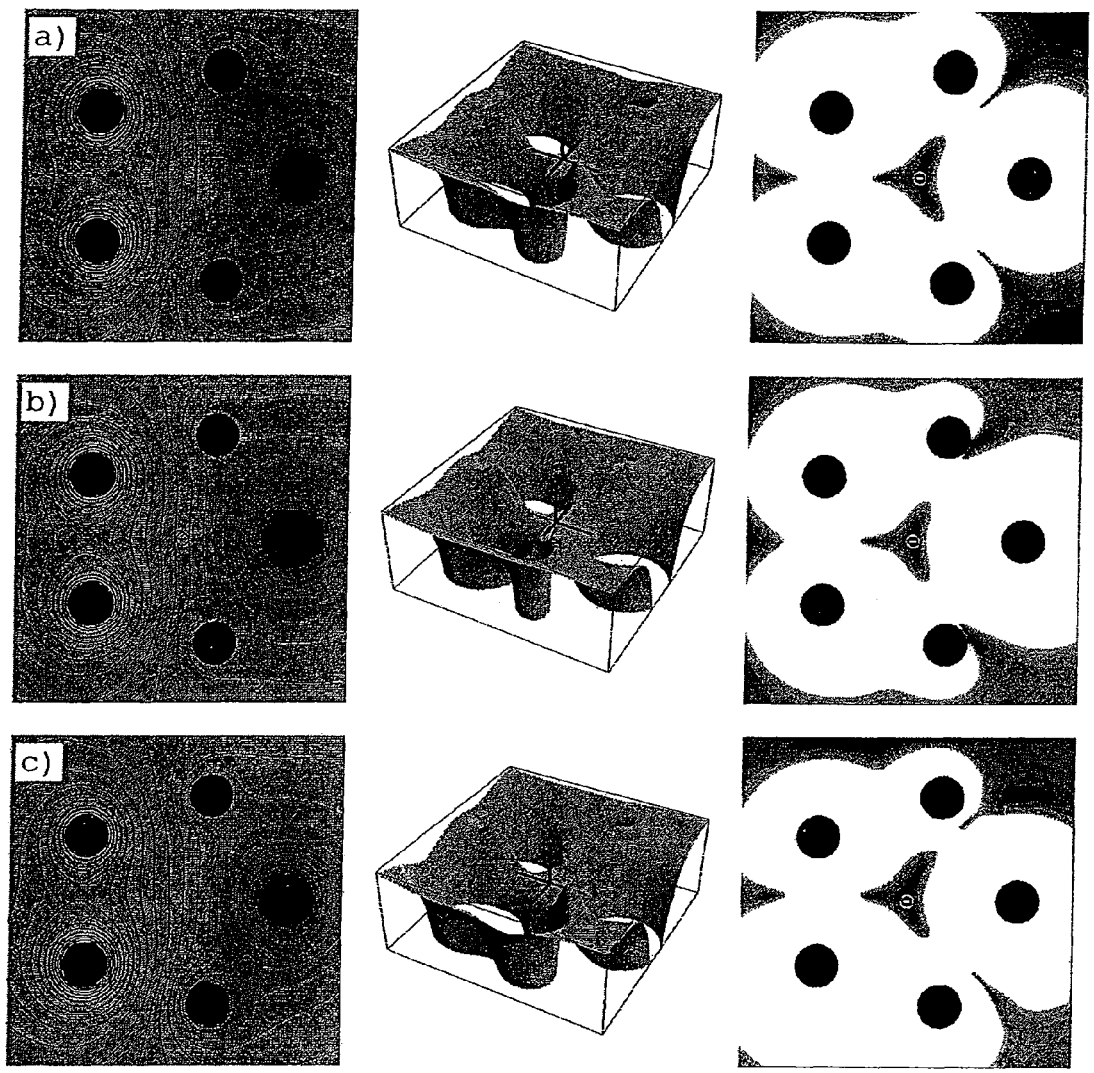
FIGS. 4(a) through (c) show a dipole held at the origin with an orientation of θ=0 by a field of 15 kV/m with force vectors of {0, 0} fN, {2, 0} fN, {0, −2} fN respectively. The first image in each part of FIG. 4 shows the voltage field in the plane. The second image in each part of FIG. 4 shows the dipole potential energy $-\alpha_{rod}\vec{E}\cdot\vec{E}$. The third image in each part of FIG. 4 shows the magnitude of difference in force between what was desired and what exists at a particular location normalized by the force required to move the rod at one rod length per second.

In FIG. 4, the concept is illustrated. The lines of constant voltage are plotted in the plane of the electrodes and the potential energy of the rod is projected on a vertical axis below. The electrode voltage set is calculated that orients a single rod at the center of the array to an angle of 45 degrees with no applied force. It is evident that the rod is oriented in the desired direction by noting the lines of constant voltage. The cross represents the rod's position on the potential energy plot. Additionally, it is apparent that there is no applied force since the potential energy has a slope of zero with respect to both the x and y axis at the rod location. It should be noted that this is an unstable equilibrium.

As stated above, the voltages that control a single particle are found using 4n+1 electrodes where the additional electrode provided an extra degree of freedom that allows the 4 constraints imposed by the angle and the force on each rod to be satisfied. A more conservative method is to use 5n electrodes and apply the 4n constraints where n is the number of particles. This gives an underdetermined system. Since the electrode voltages must be supplied by a device with its own limitations, it is to our benefit that the voltages be kept to reasonable values. Therefore, it makes sense that we should wish to minimize the sum of the squared voltages. The constraints on each rod have been put in terms of the sources (point charges, induced dipoles, etc.) on each electrode. These constraints can be reformulated into being on the voltage to be applied to each electrode through a transformation matrix. Therefore, our constraints and our goal (sum of squares of voltages) are all in terms of voltages and the problem can be solved through minimization. Minimization is generally an iterative process, and therefore slow, however in this particular case, the form of the problem allows for the method of Lagrange multipliers to be used to provide a solution directly.

In summary, we apply the 4n constraints as before, but apply to them a transformation matrix that puts them in terms of the voltages on each electrode. Making sure that we have at least 5n electrodes, we minimize the sum of the squared voltages under the constraints using the method of Lagrange multipliers. This replaces the process of generating an additional constraint, finding the sources representing each electrode, and then using these sources to calculate the voltages required on each electrode.

The geometry discussed above has been idealized. In one embodiment, the electrodes and the rods are not immersed in a single medium. Rather, the electrodes are fabricated on a glass substrate ($\in_{substrate}=4\in_0$) and the rods settle out of a suspension fluid ($\in_{medium}=80\in_0$, $\sigma_{medium}=5.5(m\cdot M\Omega)^{-1}$) that is placed over the electrodes (FIG. 3a). This creates several complications but requires no substantial changes.

The electrodes are contained at the interface between two half volumes: the substrate and the suspension fluid as shown in FIG. 5b. Due to this symmetry, for a given electrode voltage set, the electric field will be exactly as described previously. A closely related problem is the parallel plate capacitor with fixed voltages. Regardless of the permittivity and the conductivity of the medium that fills the capacitor, it is well known that the electric field will not be affected. Additionally, filling the capacitor with two parallel isotropic media yields the same electric field in each region. However, this is only true providing that no component of the electric field is normal to the interface at the interface. In the geometry in FIG. 5a, since the electrodes are contained at the interface, this condition is satisfied. Therefore, like the parallel plate capacitor, the electric field in each half volume is identical to each other and to the idealized single-medium geometry.

Unfortunately, the symmetry that applies the electrode's electric field does not apply to the nanorod. The nanorod is not truly at the interface, but rather immersed in the suspension fluid at some small distance, h, above the glass. Therefore, some portion of the electric field created by the rod's induced dipole is normal to the fluid-glass interface at the interface creating a polarization surface charge density as shown in FIG. 5c. Assuming the rod is parallel to the interface, for regions above the surface, this can be modeled as an image dipole positioned at −h below the surface with a magnitude and direction $$\vec{p}_{image} = \frac{\varepsilon_{medium} - \varepsilon_{substrate}}{\varepsilon_{medium} + \varepsilon_{substrate}} \vec{p}_{rod} = \Gamma \vec{p}_{rod}. \quad (17)$$

Note that if $\varepsilon_{medium} > \varepsilon_{substrate}$, the image dipole is of the same sign as the original and therefore the rod is repelled by its own image. The force between two orthogonal parallel dipoles is $$F_{rep} = \frac{3 p_{rod} p_{image}}{64 h^4 \varepsilon_{medium}} = \frac{3 \Gamma p_{rod}^2}{64 h^4 \varepsilon_{medium}} \quad (18)$$

The image dipole creates its own electric field at the rod location so that the actual dipole on the rod is $$\vec{p}_{rod} = \alpha_{rod} \vec{E} = \alpha_{rod} (\vec{E}_0 + \vec{E}_{image}) \quad (19)$$
$$= \alpha_{rod} \left( \vec{E}_0 - \frac{\vec{p}_{image}}{32 h^3 \pi \varepsilon_{medium}} \right)$$
$$= \alpha_{rod} \left( \vec{E}_0 - \frac{\Gamma \vec{p}_{rod}}{32 h^3 \pi \varepsilon_{medium}} \right)$$

or rather $$\vec{p}_{rod} = \vec{E}_0 \alpha_{rod} \left( 1 + \frac{\alpha_{rod} \Gamma}{32 h^3 \pi \varepsilon_{medium}} \right)^{-1} \quad (20)$$
$$= \vec{E}_0 \alpha_{rod} (1 - CF).$$

The upward repulsive force from the image dipole will quickly reach an equilibrium with the downward gravitational force so that $$F_{grav} = F_{rep} = \frac{3\Gamma}{64 h^4 \varepsilon_{medium}} \left( \vec{E}_0 \alpha_{rod} \left( 1 + \frac{\alpha_{rod} \Gamma}{32 h^3 \pi \varepsilon_{medium}} \right)^{-1} \right)^2. \quad (21)$$

Since the gravitational force is known, this can be easily solved to find h. Providing that $h \ll |\vec{R} - \vec{r}_i|$, the rod may still be approximated as being at the interface (i.e., z=0) for all the voltage field calculations. If the correction factor CF is close to zero, the induced dipole on the rod is not significantly affected by the image charge and my still be approximated as $\vec{p}_{rod} = \alpha_{rod} \vec{E}_0$.

So far, the conductivity of the suspension medium has been neglected. This is technically not necessary. Adding conductivity to either the substrate or the suspension fluid will introduce an induced current, but it can be shown that this will have no affect on the dielectrophoretic force applied to the rod. However, in practice, conduction across the interface of the suspension fluid and the electrodes is very complicated and it is difficult to support an electric field in a medium with a finite conductivity.

Every medium with some conductivity has a frequency below which it behaves essentially as a conductor and above which it behaves essentially as a dielectric. Introducing time variation to the electrodes would initially appear to be a large departure from the theory laid out so far, however it actually changes nothing. If $V_i \rightarrow -V_i$ is substituted for each electrode i, the electric field will reverse direction everywhere but it will maintain the same magnitude. Likewise, the induced dipole on the nanorod will also reverse direction. However, because the potential energy of the rod is proportional to $|\vec{E}|^2$, the force applied to the rod is unchanged.

This approach to the manipulation of individual particles can be practically implemented using a realistic range of parameters. In addition to the geometry of the electrodes, experimental parameters such as the dipole's polarizability ($\alpha_{rod}$), the applied force ($F_x$ and $F_y$), and the applied electric field ($E_0$) must be specified. An exemplary embodiment of the invention is shown in the manipulation of a gold nanorod. In this example, the gold nanorod has a length l=1.4 μm, a radius r=35 nm, and a conductivity $\sigma_{rod}=\infty$, and is suspended in deionized water at room temperature with a dynamic viscosity $\mu_{medium}=1.0$ mPa·s, a dielectric constant $\varepsilon_{medium}=80\varepsilon_0$, and a conductivity $\sigma_{medium}=5.5\times10^{-6}$ (m·Ω)$^{-1}$.

Providing that the signal applied to all electrodes is a square wave at a frequency $f_{carrier} \gg \sigma_{medium}/2\pi\varepsilon_{medium}$, the conductivity of the medium can be ignored and the water treated as a pure dielectric without adding the complication of time average fields to the derivation. While the employment of AC sources may initially seem as a departure from the theory developed in previous section, a close examination of Eqs. (13) to (16) would show that flipping the polarity of all voltages $V_i$ will result in the same dipole orientation and net applied force. The rod will be oriented along the direction of the electric field regardless of its sign. Therefore, a useful way to effectively remove the conductivity of the suspension medium is to alternate the applied voltages between positive and negative $V_i$ at a high frequency, $f_c$. Intuitively speaking, an induced dipole is oriented and attracted by a point charge in the same way regardless of its polarity.

The problem can also be treated under a "quasi-static" regime as long as the wavelength $\lambda=c/f_{carrier}$ remains much larger than any other experimental dimension. Employing square waves as sources therefore solely serves to eliminate the medium conductivity from the development. For deionized water $f_{carrier}$ should be greater than 1.2 kHz. Similar reasonable values can be found for organic solvents. However, cell culture media with conductivities on the order of 2 (m·Ω)$^{-1}$ will require $f_{carrier}$ to be greater than 450 MHz. While such range remains readily available with standard RF generators, such necessity would incur higher implementation costs due to the higher prices of such equipment.

Using a derivation found elsewhere and further approximating the rod as a prolate ellipsoid perfect conductor in a dielectric, the polarizability along the main axis yields:

$$\alpha_{rod} = \frac{4 l r^2 e^3 \pi \varepsilon_{medium}}{3(e^2-1)\left(2e - \text{Ln}\left[\frac{1+e}{1-e}\right]\right)} \quad (22)$$

where $e=\sqrt{1-r^2/(l/2)^2}$. For the particle size and conditions presented, this yields a polarizability of $\alpha_{rod}=3\times10^{-27}$ (C·m$^2$/V).

One would generally wish to apply a force generating a pre-determined translational velocity to the rod. The viscous drag coefficients relate the two and thus allows us to estimate a reasonable range of required applied force. The rod has drag coefficients such that for a fluid flow velocity $V_{fl}$ along its axis $$F_{D\parallel} = V_\parallel C_\parallel = V_\parallel \frac{2\pi\mu_{medium}l}{\text{Ln}\left[\frac{l}{r}\right] - 0.72} \quad (23)$$

and for a fluid flow velocity $V_\perp$ normal to its axis $$F_{D\perp} = V_\perp C_\perp = V_\perp \frac{2\pi\mu_{medium}l}{\text{Ln}\left[\frac{l}{r}\right] + 0.5} \quad (24)$$

For the particle size and conditions presented, this yields $C_\parallel = 5.9 \times 10^{-9}$ (N·s/m) and $C_\perp = 5.9 \times 10^{-9}$ (N·s/m). It is worth noting that the drag coefficients are relatively close in spite of an aspect ratio of twenty. Defining one rod length per second as a reasonable desired velocity, and using the parallel drag coefficient in Eq. (23) yields a required force of $F_{norm} = 4.1$fN. The steady-state velocity is reached very quickly so that one can consider the induced velocity as directly proportional to the applied force through the drag coefficients. It is therefore reasonable to take $F_x$ and $F_y$ to be some large fraction of $F_{norm}$ to maintain a velocity of a little less than one rod length per second.

The magnitude of the electric field has several constraints. The field must be strong enough to rotate the rod against viscous drag, hold the rod's orientation against Brownian motion, and hold the rod in the z=0 plane.

Ignoring Brownian motion, the slightest electric field will eventually orient the nanorod along the desired orientation. However, if the desired angle of the rod is changing and the electric field is too weak, viscous drag will prevent rod from orienting with the field. Let us therefore assume that we wish to change the orientation at a minimal rotational velocity of $f=1$ $s^{-1}$ and can tolerate a phase lag between the rod and the electric field of $\phi=\pi/8$. The torque due to the electric field is dependent on the magnitude of the electric field and the phase difference between the rod and the field. Noting that the rod is an induced dipole so only the component of the field along the major axis contributes to $p_{rod}$, the electric torque is given as:

$$|T_E| = p|E_0|\sin[\phi] = \alpha_{rod}|E_0|^2 \cos[\phi]\sin[\phi]. \quad (25)$$

The torque due to drag on a rod rotating at a frequency f can be estimated from Eq. (24) as $$T_D = \int_{-l/2}^{l/2} \frac{4\pi\mu_{medium}(2\pi fR)}{\text{Ln}\left[\frac{l}{r}\right] + 0.5} R\,dR \quad (26)$$

$$= \frac{2l^3 f\pi^2 \mu_{medium}}{3\left(\text{Ln}\left[\frac{l}{r} + 0.5\right]\right)}.$$

Assuming steady state conditions, setting Eqs. (25) and (26) equal to each other and solving for the electric field yields a lower bound on the electric field of $$E_0 > E_{rot} = \sqrt{\frac{2l^3 f\pi^2 \mu_{medium}}{3\alpha_{rod}\cos(\phi)\sin(\phi)\left(\text{Ln}\left(\frac{l}{r}\right) + 0.5\right)}} \quad (27)$$

For the conditions proposed, the value of the minimum electric field to needed to rotate the rod against viscous forces is $E_{rot} = 6.0$ (kV/m).

Since the polarizability scales with the cube of the particle size, this value is unaffected by the particle size and depends only on the particle shape. However, for nanoparticles Brownian motion can become a significant factor. Within the fluid, energy is indeed exchanged randomly between the molecules and the particles with amounts on the order of $\Delta E = k_B T$, where $k_B$ is Boltzmann's constant, and T is the temperature in Kelvin. At room temperature, this value is $\Delta E = 4.1 \times 10^{-21}$ Joules. The effects of Brownian motion are therefore estimated by comparing this thermal fluctuation energy to the energy involved in a related displacement from electrostatic equilibrium. In other words, the potential energy difference between the desired angle and a maximum tolerable displacement angle must be smaller than $\Delta E$ in order to maintain the particle's orientation against Brownian motion.

The potential energy of the nanorod oriented at an angle $\gamma$ to the electric field is $U(\gamma) = -\alpha_{rod} E_0^2 \cos(\gamma)^2$. Note that if $\gamma = 0$, then the rod is in equilibrium, aligned with $\theta$, and in agreement with Eq. (1). If an angle $\gamma_{max} = \pi/4$ is defined as the maximum tolerable displacement from $\theta$, the thermal energy required for such a displacement is $\Delta E = U(\gamma_{max}) - U(0)$. This yields a lower bound on the electric field of $$E_0 > E_{orient} = \frac{1}{\sin(\gamma_{max})\sqrt{\frac{k_B T}{\alpha_{rod}}}} \quad (28)$$

Using the given temperature, polarizability, and maximum allowable displacement, the minimum electric field to hold the rod's orientation is $E_{orient} = 4.7$ (kV/m).

While lateral (x and y) Brownian motion can be managed by applying small forces counter to the drift, vertical (z) Brownian motion can not be directly compensated. However, the electric field will decay with distance from the electrodes and, therefore the plane z=0 is a weak positive dielectrophoretic trap with respect to the z axis. Quantifying this trap is difficult because of the complex nature of the electric field generated by the electrodes. However, if each electrode is represented by only a point charge and assumed to lie on a circle of radius $\alpha$, so that the voltage field is $$V[\vec{R}] = \sum_{i=1}^{n} \frac{q_i}{4\pi\varepsilon|\vec{R} - a\{\cos(\kappa_i), \sin(\kappa_i), 0\}|} \quad (29)$$

and we further assume that the particle is at the center of the array, than it is easily shown that the potential energy of the rod is $$U[\{0,0,z\}] = -\left(\frac{1}{(1+(z/a)^2)^4}\right)\alpha_{rod} E_0^2. \quad (30)$$

Again, comparing the thermal energy to the difference in potential energy between the equilibrium position and a maximum tolerable displacement $z_{max} = 2l$ yields $\Delta E = U(z_{max}) - U(0)$. Solving for the electric field presents the condition $$E_0 > E_{z-axis} = \left(1 - \frac{1}{(1+(z_{max}/a)^2)^4}\right)^{-\frac{1}{2}} \sqrt{\frac{k_B T}{\alpha_{rod}}}. \quad (31)$$

For the electrodes spaced on a circle with a radius $\alpha=25$ μm and the conditions proposed, the minimum electric field to keep the rods near to x,y-plane is $E_{z-axis}=15$ kV/m. Since this is the most stringent constraint, the electric field required at the particle location is also $E_0=15$ kV/m.

If the thermal constraints ($E_{orient}$ or $E_{z-axis}$) are more stringent than the rotational constraint ($E_{rot}$), and the particle size is linearly scaled down, the electric field must grow with a power of 3/2 to compensate. On the other hand, if the electrode array is linearly scaled down with the particle, the voltage on the electrodes must only grow with a power of 1/2 in order to compensate.

For simulation purposes, 15 kV/m is used as the required applied electric field, and some fraction of 4.1fN as the applied force. Additionally, five spherical electrodes form an array located in the x,y-plane, centered on a circle of diameter 50 μm, each with a diameter of 10 μm. These ideas easily extrapolate to other planar structures that would be readily fabricated using standard lithography techniques.

Figure 6:
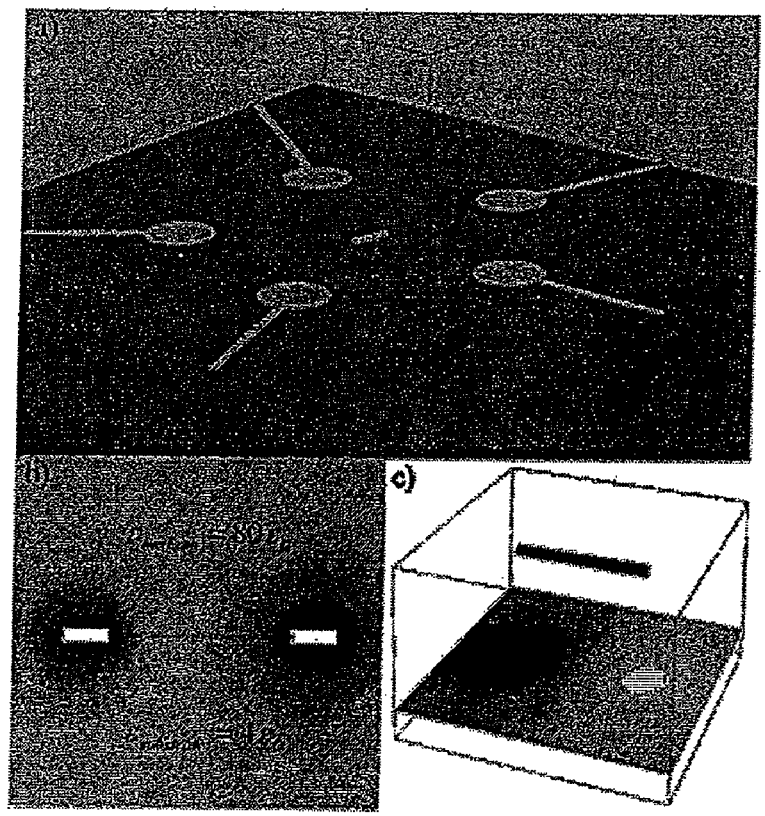
FIG. 6 shows: (a) an experimentally realizable geometry consisting of two media, the substrate on which the electrodes are fabricated and the suspension fluid which contains the particles; (b) the voltage field surrounding two electrodes in cross section demonstrating that the same electric field exists in both media; and (c) the polarization surface charge induced by the particle's dipole at the interface of the two media for an electric field in which white represents positive charge and black represents negative charge.

In FIG. 6, parts (a), (b), and (c) show a dipole held at the origin with an orientation of θ=0 by a field of 15 kV/m with force vectors of {0,0} fN, {2, 0} fN, {0,−2} fN respectively. The first image in each part of FIG. 6 shows the voltage field in the plane. The false color scale ranged from −3 V to 3 V, which is easily realized on standard waveform generator. It is therefore clear that no unreasonable voltages are required. The dipole will lie with the electric field, perpendicular to the lines of constant voltage. In each part of FIG. 6, it is also apparent that this orients the rod at θ=0, as predicted.

The second image in each part of FIG. 6 shows the dipole potential energy $-\alpha_{rod}\vec{E}\cdot\vec{E}$. The dipole lies at the center. The dipole will move in the direction in decreasing potential energy. In FIG. 6(a), the center represents an unstable balance point with no net force. In FIG. 6(b), the potential energy is sloped in the +x direction, and in FIG. 6(c) the potential energy is sloped in the −y direction as predicted.

The third column shows the magnitude of difference in force between what was desired and what exists at a particular location normalized by the $F_{norm}$, i.e. $|\vec{F}[\{x,y\}]-\vec{F}|/F_{norm}$. As discussed earlier, even in FIG. 6(a) where the force is zero, the center is a point of instability. This is readily apparent in the plots of the potential energy. Regions in white represents errors greater than one and correspond to the rod moving at a velocity greater than one rod length per second different than what was desired. In each set, there is a region several rod lengths across in which the error is substantially less than one, indicating that the rod's movement away from that point will be slow enough to allow active or user feedback to be used to control motion. This allows the rod to be balanced at that point if no motion is desired, or moved in a controlled fashion if a force is applied.

In another embodiment, there is provided a method for arbitrarily moving and orienting metallic rod-shaped particles using static electric fields. Using the control of a single nanorod as an example, suitable parameters are determined and the algorithm is simulated. The results show that the desired orientation and force is produced for a small distance around the rod. While the results also indicate that the system is unstable with regard to position, it is not so unstable as to prevent compensation through a simple feedback mechanism. This could, for example, provide a simple "touch-less" approach to the planar manipulation of nanostructures.

In another embodiment, the apparatus and method of the present invention can be generalized to a three dimensional positioning system. While localizing the particles in 3D space is more difficult, the principles are the same. In such an embodiment, the force on each particle would be put in terms of 3 constraints, namely $F_x$, $F_y$, and $F_z$, and the force of gravity must be accounted for. The angle of each particle would also be put into three constraints, namely $E_x$, $E_y$, and $E_z$. However, the nature of the constraints is the same. They remain linear and can be used as the constraints in a minimization problem.

It should be understood that every material has a frequency response in terms of its conductivity and dielectric constant. Because of this, a material which behaves like a conductor at one frequency might behave as a dielectric at another frequency. If at a particular frequency, the dielectric constant of a particle is less than that of the surrounding fluid, it will behave opposite than expected. This has been termed negative-dielectrophoresis (NDEP). This can cause particles to orient perpendicular to an electric field as opposed to parallel to it as expected. The angle of the particle is still controlled by the angle of the electric field and the force on the particle is still controlled by the gradient of the electric field. If a particle had an effectively negative polarizability, it would manifest itself in two ways. First, the particle would orient perpendicular to the applied electric field. Second, the particle would feel a force opposite that of a positively polarizable particle. However, both these behaviors would still result in four linear constraints and would be dealt with in the same way. Examples of such particles are cells which can have negative polarizabilities at some frequencies.

Stated more broadly, the polarizability of the particle is the effective polarizability, which takes into account the affect of the surrounding fluid and the particle material at the applied frequency. The polarizability along each axis may in fact even be negative. The particle will align such that the axis with the greatest polarizability is aligned with the electric field, even if this is the axis with the least negative polarizability. The applied force, which includes a factor of the polarizbility, will be toward the region of greater field if this term is positive, and toward the region of less field if this term is negative.

In order to better understand the present invention, the following non-limiting examples are presented.

EXAMPLES

Figure 5:
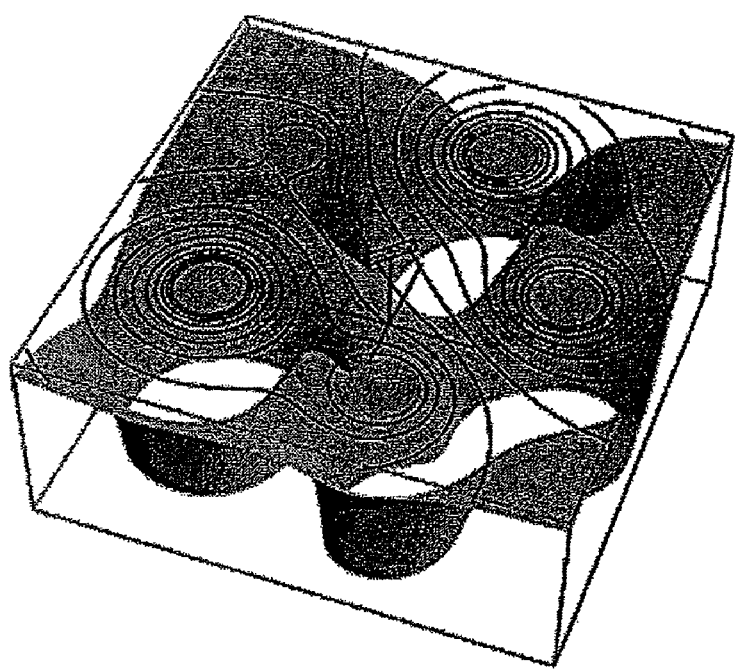
FIG. 5 shows an electrode voltage set that orients a nanorod at the center of an electrode array to an angle of 45 degrees with no applied force. The lines of constant voltage are shown for the plane of the array in black. The potential energy for the same plane is projected on the vertical axis below. The cross represents the rod's position on the potential energy plot.
Figure 7:
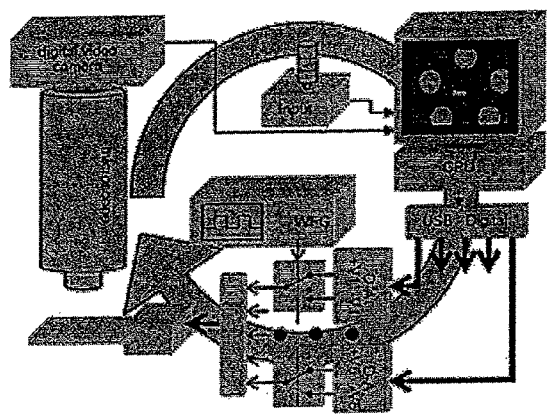
FIG. 7 shows the architecture of an embodiment of the experimental apparatus.

An embodiment of the experimental apparatus is presented. In this example, the rod is in an unstable equilibrium as shown in FIG. 5. In order to prevent the rod from catastrophically drifting, the particle must be controlled using a negative feedback loop. This is illustrated in FIG. 7. Here the components will be discussed, beginning at the particles and tracing this loop backwards.

Gold nanorods with a length of 6 μm and a diameter of 300 nm were created using electrochemical template synthesis. They were repeatedly rinsed and suspended in deionized water.

The electric field was generated by five electrodes, each 40 μm in diameter and equally spaced on a 200 μm circle. They were fabricated on a microscope slide using 200 nm of gold and a 50 nm chrome sticking layer using standard lithographic and etching techniques. The microscope slide was pretreated in oxygen plasma to promote wetting. This helped keep the nanorods mobile at the surface by minimizing hydrophobic exclusion. A drop nanorod suspension was placed onto the electrode set and was sealed using a silicone spacer and a coverslip. The rods quickly settled out of suspension and demonstrated Brownian motion at the glass interface.

The electrodes were connected to contact pads that were sized and spaced to allow direct integration with an edge-card adapter. This provided a convenient method to apply voltages to each electrode without the need for a probing station.

The voltages for each of the five electrodes was generated by five 8-bit digitally controlled potentiometers, each providing two lines at potentials of $+V_i$ and $-V_i$. Note that $+V_i$ may be positive or negative. Five high speed multiplexers switched between these two voltages at frequency $f_c$, to produce the five square-wave signals. The digital potentiometers were attached to a USB-digital output board which was controlled through a Labview application.

The Labview application calculated the proper electrode voltages using the input from the user and real-time video of the nanorod and electrodes. It also recorded and displayed all necessary information. Video was captured by firewire camera attached to a microscope.

The application overlaid five circles onto the video provided by the camera. The program is spatially calibrated by properly aligning the circles with the electrodes. The application also overlaid a cursor onto the image that specifies $\vec{R}$. If the cursor is properly centered on a nanorod, that nanorod will exhibit the orientation and be influenced by the force specified by the user. The user can move the cursor to a specific nanorod, or the program can automatically place the cursor on the brightest spot within a region of interest. The latter provides an effective method of tracking a rod and calculating the electric field for the location of the rod even as that rod is moving. The application's main loop cycled at 7.5 Hz.

The application had three modes of operation. The user input could either direct the force, the velocity, or the position. Since the velocity can be related to the force, the second mode relies on the first. In the third mode, the user specifies a target location on the plane. The difference between two points, namely the target location and the location of the rod, can be regarded as a desired velocity. Using simple negative feedback, the application continually attempts to bring the rod back to the target location. Again, this mode indirectly relies on controlling the force. Therefore all three modes use the formulation presented in the equations above. Additionally, the target location can be changed using a program to induce motion along specified paths.

The geometry of the electrodes, medium properties, and particle size all impose constraints on experimental parameters such as reasonable electric field magnitude, frequency, and force magnitude. The gold nanorods had a length $l=6$ μm, a radius $r=300$ nm, and a very large conductivity which will be approximated as $\sigma_{rod}=\infty$. They were suspended in deionized water at room temperature with a dynamic viscosity $\mu_{medium}=1.0$ mPa·s, a dielectric constant $\epsilon_{medium}=80\epsilon_0$, and a conductivity $\sigma_{medium}=5.5$ (m·MΩ)$^{-1}$. The electrodes were fabricated on a glass slide with a dielectric constant $\epsilon_{substrate}=4\epsilon_0$ Providing that the signal applied to all electrodes at a frequency $$f_{carrier} \gg \sigma_{medium}/(2\pi\epsilon_{medium})=1.2 \text{ kHz}, \quad (32)$$

the conductivity of the medium can be ignored. A signal of 500 kHz is therefore considered sufficient.

A derivation found in A. H. Sihvola, *Electromagnetic mixing formulas and applications* (Institution of Electrical Engineers, London, 1999), which is incorporated herein by reference, was used. Further approximating the rod as a prolate ellipsoid perfect conductor in a dielectric, the polarizability along the main axis yields:

$$\alpha_{rod} = \frac{4lr^2 e^3 \pi \epsilon_{medium}}{3(e^2-1)\left(2e - \text{Ln}\left[\frac{1+e}{1-e}\right]\right)} \quad (33)$$

$$= 30.\times 10^{-27}\left(\frac{C \cdot m^2}{V}\right),$$

where $$e = \sqrt{1 - r^2/(l/2)^2}.$$

The viscous drag coefficients relate the force and velocity. The rod has drag coefficients such that for a fluid flow velocity $V_\square$ along its axis $$F_{D\square} = V_\square C_\square = V_\square \frac{2\pi\mu_{medium}l}{\text{Ln}\left[\frac{l}{r}\right] - 0.72} \quad (34)$$

$$= V_\square\left(13.\times 10^{-9}\left(N \cdot \frac{s}{m}\right)\right)$$

and for a fluid flow velocity $V_\perp$ normal to its axis $$F_{D\perp} = V_\perp C_\perp = V_\perp \frac{2\pi\mu_{medium}l}{\text{Ln}\left[\frac{l}{r}\right] + 0.5}. \quad (35)$$

$$= V_\perp\left(9.0\times 10^{-9}\left(N \cdot \frac{s}{m}\right)\right)$$

Defining one rod length per second as a reasonable desired velocity, the drag coefficient may be selected to yield a required force of $F_{norm}=76$fN. The steady-state velocity is reached very quickly so that one can consider the induced velocity as directly proportional to the applied force through the drag coefficients. It is therefore reasonable to take $F_x$ and $F_y$ to be some large fraction of $F_{norm}$ to maintain a velocity of a little less than one rod length per second.

Ignoring Brownian motion, the slightest of electric field will eventually orient the nanorod along the desired orientation. However, if the desired rod angle is changing and the applied torque is too low the rod may never properly orient. It is therefore assumed that the orientation is changed at a minimal rotational velocity of $f=1$ (s$^{-1}$) and tolerating a phase lag between the rod and the electric field of $\phi=\pi/8$. The torque due to the electric field is dependent on the magnitude of the electric field and the angular phase difference between the rod and the field $\phi$. Noting that the rod is an induced dipole so only the component of the field along the major axis contributes to $P_{rod}$ the electric torque is given as:

$$|T_E|=p_{rod}|E|\sin[\phi]=\alpha_{rod}|E|^2\cos[\phi]\sin[\phi]. \quad (36)$$

The torque due to drag on a rod rotating at a frequency f can be crudely estimated as $$T_D = \int_{-l/2}^{l/2} \frac{4\pi\mu_{medium}(2\pi fR)}{\text{Ln}\left[\frac{l}{r}\right]+0.5} R\, dR \quad (37)$$

$$= \frac{2f\pi^2 \mu_{medium}}{3\left(\text{Ln}\left[\frac{l}{r}\right] + 0.5\right)}.$$

Assuming steady state conditions, setting (36) and (37) equal to each other and solving for the electric field yields $E_0 = 6.0$ kV/m.

For the purposes of experiments to follow, 10 kV/m will be considered as a reasonable applied electric field, and some fraction of 76fN as a reasonable applied force.

Additionally, an array of five electrodes is used located in the x-y plane, centered on a circle of diameter 200 µm, each with a diameter, $d_{elec}$, of 40 µm. Approximating the electrodes as infinitely conductive very thin oblate spheroids, the capacitance and polarizability of the electrodes are $$C_i = 4d_{elec} \in_{fluid} = 110.(fC/V) \tag{38}$$

$$\alpha_{xi} = \alpha_{yi} = (2d_{elec}^3 \in_{fluid})/3 = 30. \times 10^{-24} \, C \cdot m \tag{39}$$

To determine the equilibrium height, h, of a nanorod above the surface, its weight must be determined. The specific gravity of gold is 19.3 and, by definition, the specific gravity of water is 1. Approximating the nanorod as a cylinder yields a downward force of $4.2 \times 10^{-15}$ N. Using eq. (11), h is determined to be 4.4 µm. Assuming the rod is near the center of the array, this is sufficiently small to approximate the rod at $z=0$. Using Eq. (20), at this height the electric field created by the image charge at the surface decreases the induced dipole on the nanorod by less than 1% so the dipole may still be approximated as $\vec{p}_{rod} = \alpha_{rod} \vec{E}_0$.

Figure 8:
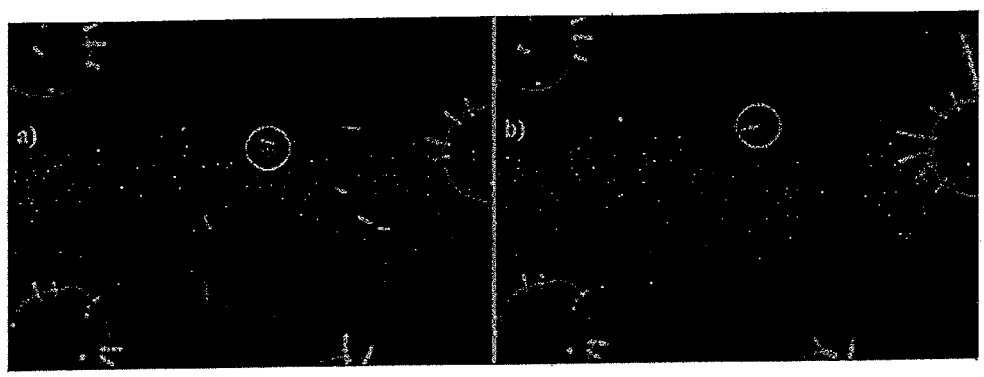
FIGS. 8 (a) and (b) show a dispersion of several rods within an array of five electrodes (electrode 2 and 5 are not seen in the picture).

A dilute suspension of rods was placed over the electrode array and the rods quickly settled to the glass substrate as shown in FIG. 8(a). Within the region bounded by the electrode array there were seven rods. The cursor, indicating $\vec{R}$, was placed over one of the rods near the center of the array. When the electrodes were activated, the indicated rod quickly aligned with the electric field. Being in regions of strong potential field gradient, all other rods quickly moved to nearby electrodes. However, the indicated rod remained balanced as shown in FIG. 8(b). As the rod drifted due to Brownian motion and small errors in modeling, the program tracked the rod's position through the microscope camera and image analysis, continually updating the point, $\vec{R}$, for which the electric field constraints are to be calculated.

Figure 9:
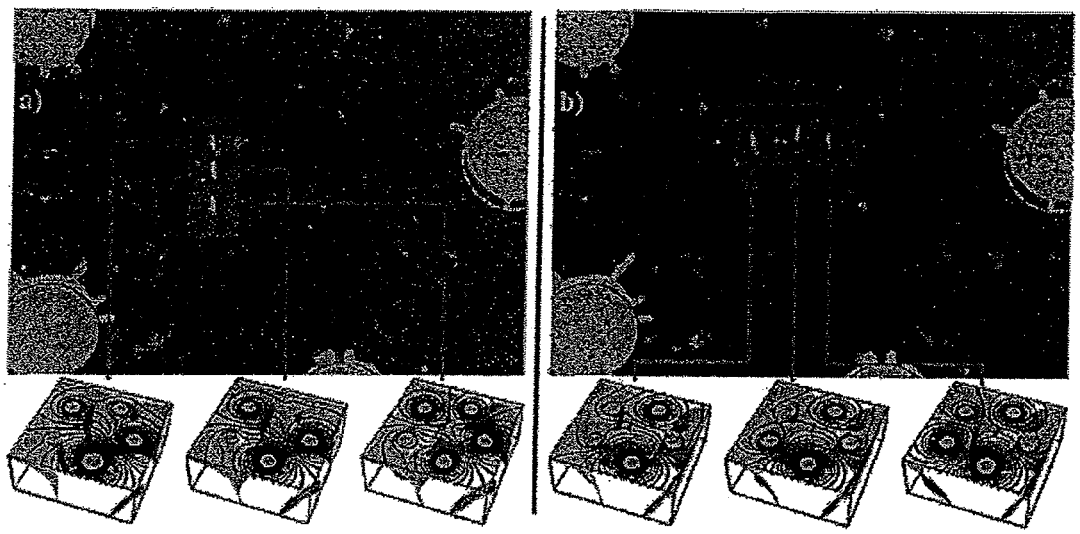
FIG. 9 shows superposition of three images of the same rod separated by several seconds while the rod experienced a force in the −y (a) and +x (b) directions to determine the parallel and perpendicular drag coefficients respectively. The field simulations below show a probable electric field and potential energy for the three moments at which the images were captured.

The rod was oriented at 90 degrees so that forces applied in the y direction are parallel to the rod orientation and forces along the x direction are perpendicular to the rod orientation. Forces in the x and y directions were applied to move the rod around the array while observing the resulting motion. Averaging the ratio of the velocity to the force in the y direction, yields an experimental parallel drag coefficient of $21. \times 10^{-9}$ (N·s/m) which is reasonably close to the theoretical value in Eq. (34) as shown in FIG. 9(a). Additionally, averaging the ratio of the velocity to the force in the x direction yields an experimental perpendicular drag coefficient of $15. \times 10^{-9}$ (N·s/m) which is close to the theoretical value in Eq. (35) as shown in FIG. 9(b).

Since the rod has different drag coefficients perpendicular and parallel to its axis, applying an oblique force will not yield a velocity in the same direction. To determine the proper force to yield a specific velocity, we first project the desired velocity into a parallel and perpendicular component, employ Eq. (15) and Eq. (16) to find the required force parallel and perpendicular to the rods axis, and then project these forces back onto the normal x-y axes.

$$\{F_x, F_y\} = M_{-\theta} \cdot \begin{pmatrix} C_\square & 0 \\ 0 & C_\perp \end{pmatrix} \cdot M_\theta \cdot \{V_x, V_y\} \tag{40}$$

where $$M_\theta = \begin{pmatrix} \cos(\theta) & \sin(\theta) \\ -\sin(\theta) & \cos(\theta) \end{pmatrix}$$

Figure 10:
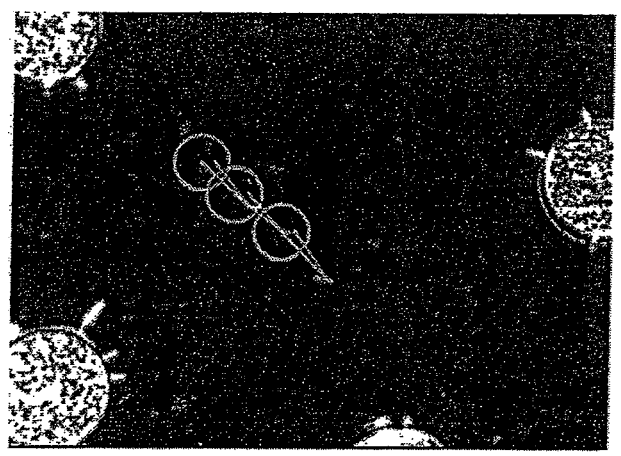
FIG. 10 shows superposition of three images of the same rod separated by 6 seconds while the rod was directed to move directly to the upper-left. Note that the rod follows the path of the directed velocity, not the force as indicated by the co-linear lines.

The rod was directed to move at an angle of 45 degrees to its orientation. In FIG. 10 it can be seen that the force and velocity are not in the same direction, but if the force is chosen carefully, the velocity may be specified in controlling a nanorod. This is evident as the rod appears several seconds later along the path of specified velocity, not vector of the force.

Approximate velocity can be defined as the difference between two positions divided by time. Given a target position $\vec{R}_T$, the velocity needed to return a rod to this point is $\{V_x, V_y\} = (\vec{R}_T - \vec{R})/(\alpha T)$, where T is the time between cycles of the program and $\alpha$ is a damping factor between 1 and 2 to prevent over compensation.

Figure 11:
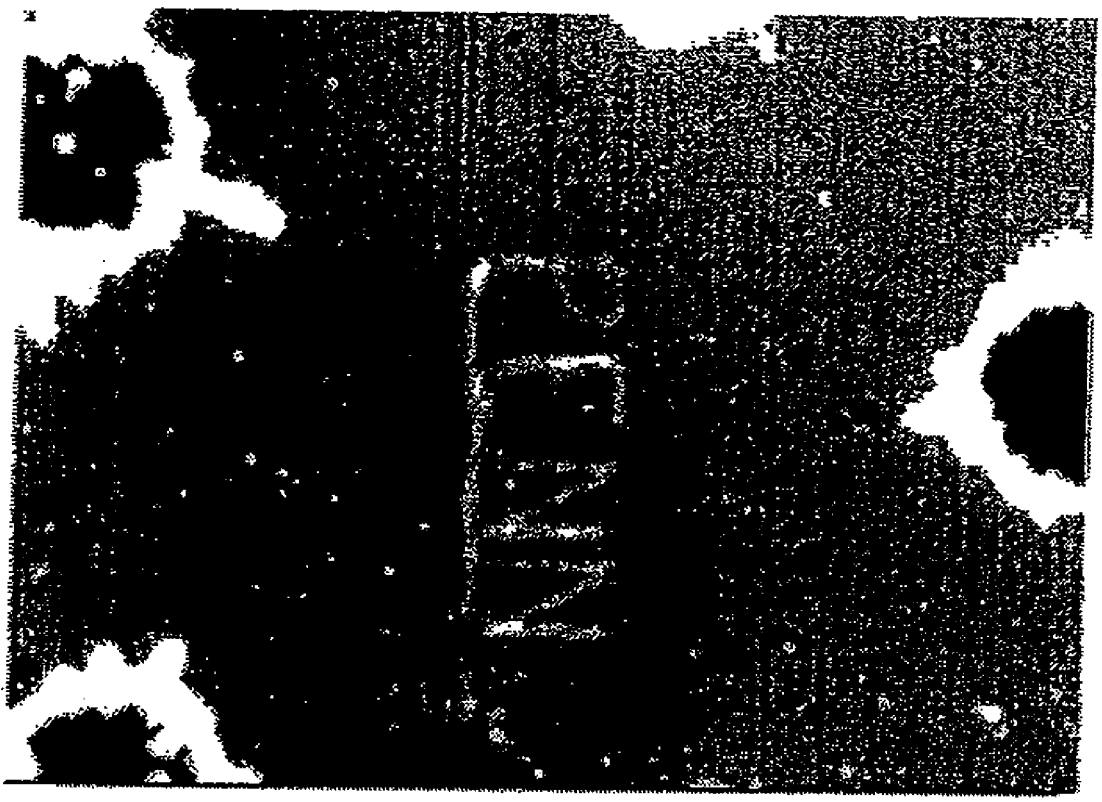
FIG. 11 shows superposition of several hundred images of the same rod separated by 1 second while the rod was directed to move along a complex preprogrammed path.
Figure 12:
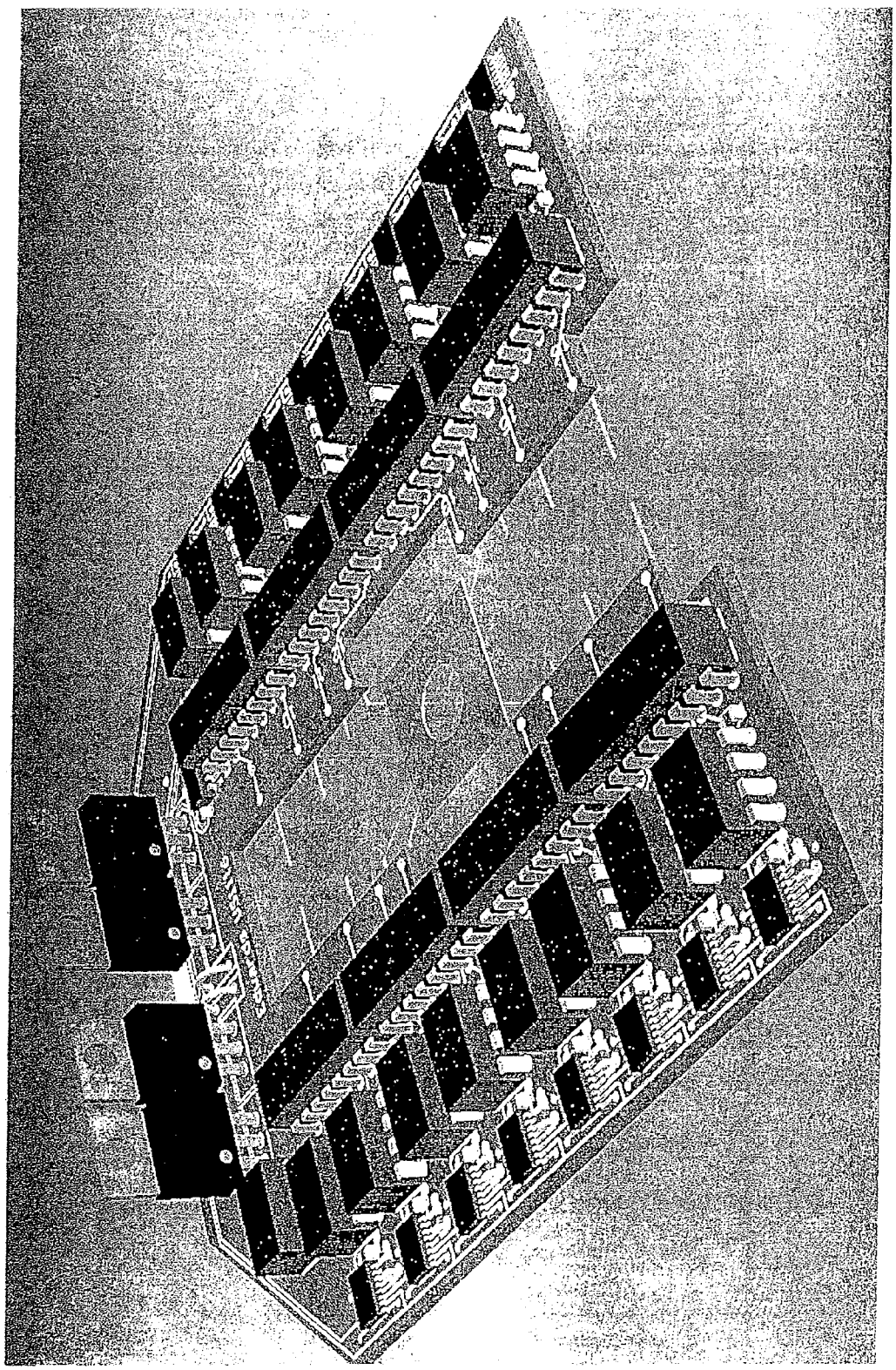
FIG. 12 shows an embodiment of a circuit suitable for use in the present invention.

By using image analysis, the position of the rod can constantly be compared to the target position and using Eq. (40), a force can be calculated that will return the rod to that location. It is evident in FIG. 10 that this represents a stabilizing negative feed back loop. It is also evident in FIG. 8 that this is necessary because even when no force is being applied, the rod is only meta-stable. Brownian motion and modeling noise are sufficient to disturb the rod out of this equilibrium position, however the negative feedback loop allows a rod to be balanced indefinitely. The target position can be a function of time and defined as $\vec{R}_T(t)$ with an associated $\theta(t)$ to allow complex paths to be preprogrammed as shown by way of example in FIG. 11.

The basic architecture of a square wave generator consists of two DC voltage sources and high speed multiplexer, also known as a mux or switch, which rapidly switches between them. To feed an array of 16 electrodes, 16 waveform generators would be required which would be prohibitively expensive and cumbersome. Each generator would need to communicate with a controller, but would need to be connected directly to each other to maintain the synchronization required to move the particles.

In one embodiment, a circuit can be used to realize higher frequencies on the electrode array. The circuit consists of an array of 16 square wave generators on a PCB board situated around a microscope slide. In this fashion, the leads carrying the high frequency signals are extremely short. As they' are all driven by the same programmable clock, they are all synchronized by default. Each generator consists of a serial input digital to analog converter which feeds into an opamp which produces specified analog voltage. This voltage is inverted and buffered so to produce two lines at, for example, 3.3(V) and −3.3(V). A high speed mux switches back and forth between these signals at rate given by clock signals. The resulting signal is fed onto the microscope slide. The clock signal is produced by a serial input clock generator chip. The same clock controls each of the 16 muxes so that they are synchronized by default. The board will have microcontroller which is used to take instructions from the computer (either via serial port or USB) and then relay these instructions to the clock generator and the 16 D-A converters. The current design can also use microcontroller on a microcontroller evaluation board.

Since the PCB board is surrounding the microscope slide where the particles are being manipulated, special considerations must be taken with respect to stray electric fields. While not required, the formulation was based on the world "infinitely" far away being at 0(V). Given that the whole electrode array is only a couple hundred microns across, "infinity" is not far away, and the upper and lower planes of the PCB board are preferably grounded to prevent the internal power planes from producing any field. In an alternate embodiment, a grounded power plane is routed onto the microscope slide to help shield the field of the particles from stray fields the produced by the board.

Possible applications of this technology include lab-on-a-chip, heterogeneous integration of electronic components, and microfluidic studies. Different objects respond to different electric field frequencies. Therefore, at certain frequencies a class of objects such as, for example, biomaterials such as cells or non-biological materials such as non-metallic particles will be unaffected by the electric field while another class of objects such as, for example, metal nanorods will remain affected. This provides two different means of moving objects. First, objects can be moved by the electric field directly and several objects may be manipulated at the same time. Ultimately, such applications are limited by the number of electrodes that can be brought within a reasonable distance to the objects. Second, a class of objects can be rendered effectively impervious to the field by carefully choosing the applied frequency and by physically moving them by an object from another class. The latter can be done in a number of ways. In one embodiment, the controlled item can externally push an object that is itself unresponsive to the applied field. In another embodiment, the controlled item can be inserted into an object that is itself unresponsive to the applied field and then moved by the movement of the controlled item. In either of these exemplary embodiments, only one object is being manipulated at a time allowing a much larger number of objects to be eventually manipulated by a single item with a small number of electrodes.

Another application of the present invention relates to heterogeneous integration of micro and nano components through directed assembly. Components which do not fit into the fabrication method of a bulk circuit could be built elsewhere, dispersed onto the substrate surface, and positioned. Once positioned, they could be protected by a passive layer, and then connected to the existing circuit through a metalization step.

Another application of the present invention relates to cell sorting. In such application, cells may be tagged using, for example, fluorescence for determination of interest. Cells of interest could then be directed in one direction while other cells could be directed in another. In this manner, for example, infected cells could be separated from non-infected cells.

A further application of the present invention relates to drug delivery. While exposing cells to a potential drug is easy, determining whether the drug has penetrated the cellular membrane is not. In one embodiment, nanoparticles can be coated with an active reagent and then pushed into fixed cells using the electric tweezers. In another embodiment, cells could be pushed onto fixed nanoparticles. In either embodiment, the introduction of the potential drug into the intracellular fluid could be accomplished.

In yet a further embodiment, the present invention can be employed in applying a force. One of the advantages of electric tweezers over optical tweezers is that optical tweezers specify a location that the manipulated particle is attracted to while the electric tweezers of the present invention specify a force at a location in space. As a result, the present invention is more suitable for experimental techniques that wish to determine the reaction of some quantity against a force.

Another embodiment of the present invention is directed to determining friction and drag coefficients of nanoparticles. By applying a known force using the electric tweezers and observing the resulting velocity of a nanoparticle, the friction and drag coefficients associated with such nanoparticle can be determined. This application can provide fundamental information on how fluids interact with surfaces and particles on the nanoscale.

Another embodiment of the present invention is directed to determining membrane stiffness. By pushing a nanoparticle against a deformable membrane such as a cellular membrane and observing the deflection, it is possible to determine the stiffness of the membrane. This application may be a useful diagnostic tool for identifying cells of interest within the context of research, diagnosis and/or treatment.

We claim:

1. A method for manipulating N particles using electric field angle and dielectrophoretic forces generated by an array of at least 4N+1 electrodes, comprising the steps of a programmed controller calculating constraints on electrode voltages to be applied to said at least 4N+1 electrodes as a function of angle of the electric field and induced dielectrophoretic force of each particle and applying a set of electrode voltages within the calculated constraints to said at least 4N+1 electrodes, wherein the positions and velocities of the N particles are manipulated by said set of electrode voltages applied to the at least 4N+1 electrodes, wherein the N particles are arbitrarily moved and oriented and/or particle drift of the N particles is countered through application of the electric field to the N particles by the 4N+1 electrodes, and wherein N is a positive integer.

2. The method of claim 1, wherein the forces applied to the particles are controlled.

3. The method of claim 1, wherein the velocities of the particles are controlled.

4. The method of claim 1, wherein the positions of the particles are controlled.

5. The method of claim 1, wherein the electrode voltages applied to the 4N+1 electrodes specify a force on a particle at an arbitrary location in space using dielectrophoretic forces generated by the 4N+1 electrodes in response to the electrode voltages applied thereto.

6. A device for the manipulation of N particles using dielectrophoretic forces and electric field angle, comprising an array of at least 4N+1 electrodes capable of applying an electric field to the N particles, and a controller programmed to calculate constraints on electrode voltages to be applied to said at least 4N+1 electrodes as a function of angle of the electric field and induced dielectrophoretic force of each particle and to apply a set of electrode voltages within the calculated constraints to said at least 4N+1 electrodes, wherein the positions and velocities of the N particles are manipulated by said set of electrode voltages applied to the at least 4N+1 electrodes, wherein the N particles are arbitrarily moved and oriented and/or particle drift of the N particles is countered through application of the electric field to the N particles by the 4N+1 electrodes, and wherein N is a positive integer.

7. The device of claim 6, wherein the particles are biological cells.

8. The device of claim 6, wherein the particles are provided in a suspension medium.

9. The device of claim 6, wherein the array is a two-dimensional array.

10. The device of claim 6, wherein the array is a three-dimensional array.

11. The device of claim 6, wherein the manipulation of the particles controls the forces applied to the particles.

12. The device of claim 6, wherein the manipulation of the particles controls the velocities of the particles.

13. The device of claim 6, wherein the manipulation of the particles controls the positions of the particles.

14. The device of claim 6, wherein the particles are disposed within objects outside the applied electric field.

15. The device of claim 6, wherein the particles are external to objects outside the applied electric field.

16. The device of claim 6, wherein the particles are nanoparticles.

17. The device of claim 16, wherein the particles are nanorods.

18. The device of claim 6, wherein the electrodes are provided on a glass substrate.

19. The device of claim 18, wherein the glass substrate is a microscope slide.

20. The device of claim 6 wherein the programmed controller comprises an edge-card adapter and a USB digital output board controlled by a processor programmed with a calculation application, further comprising contact pads that are connected to the electrodes and sized and spaced to allow direct integration with the edge-card adapter.

21. The device of claim 20 further comprising 4N+1 potentiometers responsive to said USB digital output board to generate said electrode voltages, wherein each potentiometer generates a voltage applied to an electrode.

22. The device of claim 21 wherein the outputs of the USB-digital output board are applied to the potentiometers.

23. The device of claim 22 further comprising 4N+1 multiplexers that switch the potentiometers between respective positive and negative voltages to produce square-wave signals.

24. A method for determining the coefficient of friction of a particle, comprising the steps of applying a force to the particle with the device of claim 6, and observing the resulting velocity of the particle.

25. A method for determining the drag coefficient of a particle, comprising the steps of applying a force to the particle with the device of claim 6, and observing the resulting velocity of the particle.

26. A method for determining the stiffness of a cell membrane, comprising the steps of applying a force to the membrane with the device of claim 6, and observing the resulting deflection of the membrane.

* * * * *